US012514752B2

(12) United States Patent
Teuma et al.

(10) Patent No.: US 12,514,752 B2
(45) Date of Patent: Jan. 6, 2026

(54) PATIENT INTERFACE DEVICE FOR OPHTHALMIC LASER PROCEDURES

(71) Applicant: Lensar, Inc., Orlando, FL (US)

(72) Inventors: E. Valaski Teuma, Orlando, FL (US); John McWhirter, Winter Park, FL (US); Richard Ty Olmstead, Oviedo, FL (US)

(73) Assignee: Lensar, Inc., Orlando, FL (US)

( * ) Notice: Subject to any disclaimer, the term of this patent is extended or adjusted under 35 U.S.C. 154(b) by 0 days.

(21) Appl. No.: 18/111,776

(22) Filed: Feb. 20, 2023

(65) Prior Publication Data

US 2023/0310215 A1 Oct. 5, 2023

Related U.S. Application Data

(63) Continuation of application No. 15/979,278, filed on May 14, 2018, now Pat. No. 11,583,446, which is a continuation of application No. 14/444,339, filed on Jul. 28, 2014, now Pat. No. 9,968,485.

(60) Provisional application No. 61/859,725, filed on Jul. 29, 2013.

(51) Int. Cl.
*A61F 9/009* (2006.01)

(52) U.S. Cl.
CPC .................................... *A61F 9/009* (2013.01)

(58) Field of Classification Search
CPC ............ A61F 9/009; A61F 2009/00865; A61F 2009/0087; A61F 2009/00887; A61F 9/00825
See application file for complete search history.

(56) References Cited

U.S. PATENT DOCUMENTS

| | | | | | |
|---|---|---|---|---|---|
| 2004/0267294 | A1* | 12/2004 | Will | A61B 17/0231 | 606/1 |
| 2008/0183159 | A1* | 7/2008 | Preuss | A61F 9/009 | 606/4 |
| 2011/0022035 | A1* | 1/2011 | Porter | A61F 9/00825 | 606/4 |
| 2011/0190739 | A1* | 8/2011 | Frey | A61F 9/009 | 606/4 |

* cited by examiner

*Primary Examiner* — Katherine Shi
(74) *Attorney, Agent, or Firm* — Glen P. Belvis; Belvis Law, LLC.

(57) ABSTRACT

A patient interface device for use with a laser surgery apparatus, the device including an upper assembly and a lower assembly attached to the upper assembly. The device including a spherical-like object that engages the lower assembly so that an enclosed volume is defined between the spherical-like object, the lower assembly and the upper assembly, wherein a first liquid substantially fills the enclosed volume. The device further including a channel that contains a second fluid that is exposed to ambient atmosphere.

12 Claims, 6 Drawing Sheets

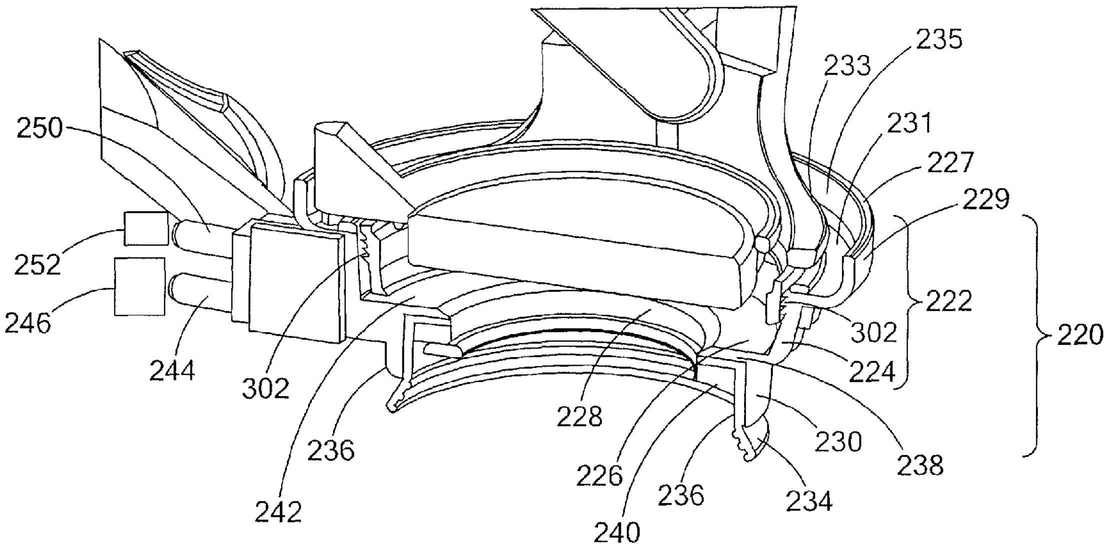
FIG. 4
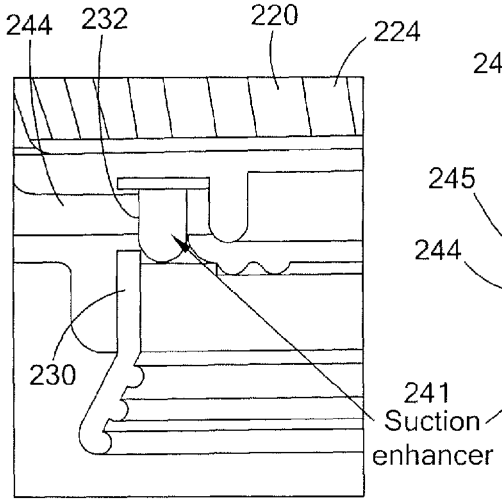
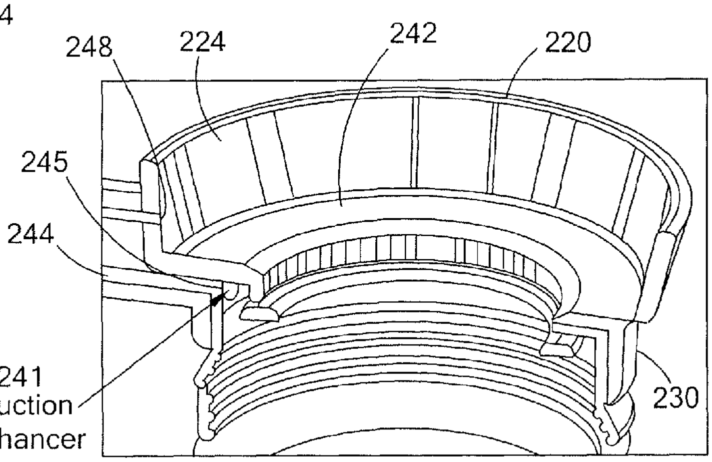
FIG. 5
FIG. 6

PATIENT INTERFACE DEVICE FOR OPHTHALMIC LASER PROCEDURES

This application is a continuation of patent application Ser. No. 15/979,278, filed May 14, 2018, which application is a continuation of patent application Ser. No. 14/444,339, filed Jul. 28, 2014, which application claims pursuant to 35 U.S.C. § 119(e) the benefit of priority of provisional application Ser. No. 61/859,725 filed Jul. 29, 2013, the entire disclosure of each of which is incorporated herein by reference.

BACKGROUND OF THE INVENTION

Field of the Invention

The present invention relates to a patient interface device for use in laser surgery on the eye.

SUMMARY

One aspect of the present invention regards a patient interface device for use with a laser surgery apparatus, the device including an upper assembly and a lower assembly attached to the upper assembly, wherein the upper assembly and the lower assembly define a volume of space. The lower assembly includes a portion that extends toward the volume of space and a suction enhancer that faces the portion and is positioned further from a centroid of the volume of space than the portion. The device further including a vacuum port formed in the lower assembly, wherein the vacuum port defines an opening that is in fluid communication with a vacuum source and the volume of space. In addition, at the vacuum port, the portion and the suction enhancer contact each other along a linear area.

A second aspect of the present invention regards patient interface system for use with a laser surgery apparatus, the device including an upper assembly and a lower assembly attached to the upper assembly, wherein the upper assembly and the lower assembly define a volume of space. The lower assembly includes a portion that extends toward the volume of space and a suction enhancer that faces the portion and is positioned further from a centroid of the volume of space than the portion. The system further including a vacuum port formed in the lower assembly, wherein the vacuum port defines an opening that is in fluid communication with a vacuum source and the volume of space. In addition, at the vacuum port, the portion and the suction enhancer contact each other along a linear area. The system further including a spherical-like object that engages the lower assembly and the portion so that an enclosed volume is defined between the spherical-like object, the portion and the lower assembly that contains a gas, wherein the vacuum port is in fluid communication with the enclosed volume and the vacuum source removes the gas from the enclosed volume.

A third aspect of the present invention regards a patient interface device for use with a laser surgery apparatus, the device including an upper assembly and a lower assembly attached to the upper assembly. The device including a spherical-like object that engages the lower assembly so that an enclosed volume is defined between the spherical-like object, the lower assembly and the upper assembly, wherein a first liquid substantially fills the enclosed volume. The device further including a channel that contains a second fluid that is exposed to ambient atmosphere.

BRIEF DESCRIPTION OF THE DRAWINGS

FIG. 4 shows a perspective and cutaway view of a portion of the patient interface device of FIGS. 2-3;

FIG. 5 shows an enlarged view of a portion of the patient interface device of FIGS. 2-4;

FIG. 6 shows a portion of the patient interface device of FIGS. 2-4;

DESCRIPTION OF THE DRAWINGS AND THE PREFERRED EMBODIMENTS

Figure 1:
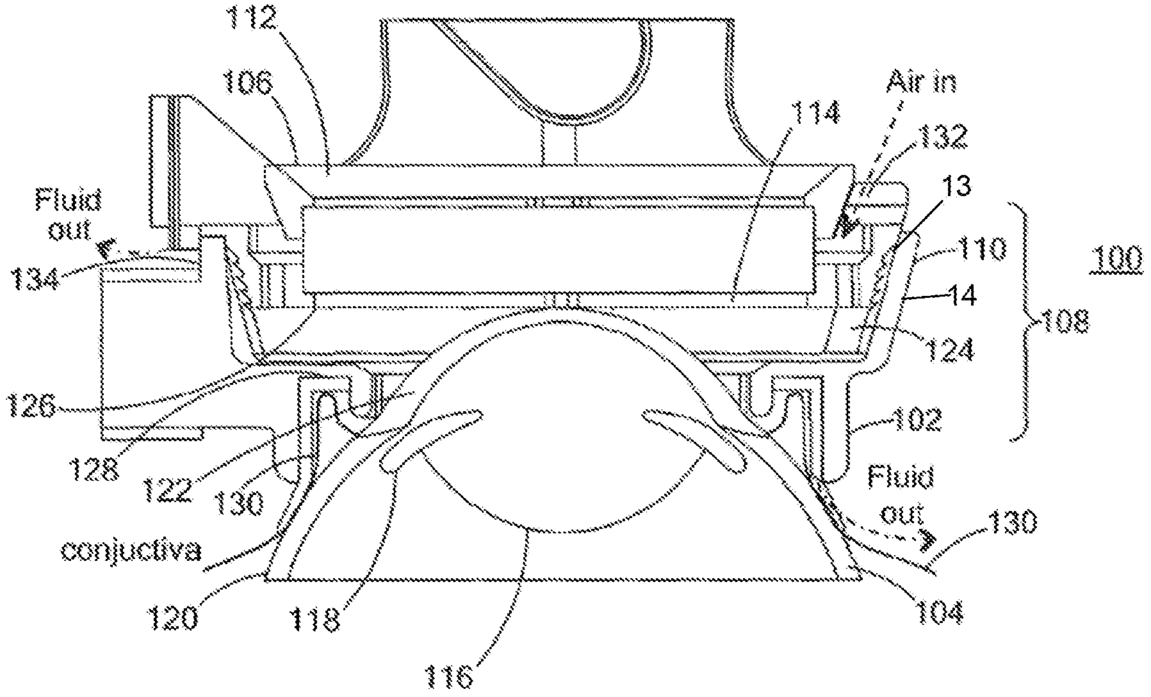
FIG. 1 shows a cross-sectional view of a portion of a first embodiment of a patient interface device.

An embodiment of a patient interface device 100 for the use in the performance of ophthalmic laser surgery is shown in FIG. 1. In particular, the patient interface device 100 includes a distal or bottom end 102, which engages an eye 104, and a proximal or top end 106, which is disposed toward a laser apparatus (not shown). The device 100 has a ring shaped structure 108 that includes an outer structure 110, an inner structure 112, and a glass plate 114. The outer structure 3 has an inner surface 13 and an outer surface 14.

As shown in FIG. 1, the device 100 is placed on an eye 104. The relative size and position of the device 100 on the eye 104 is shown with respect to the lens 116, iris 118, sclera 120, and cornea 122.

A fluid reservoir 124 is formed by the bottom 126 of the glass plate 114 and the inner surface(s) of the ring structure (s). The components of the reservoir 124 are connected together in a manner that is fluid tight. The reservoir 124 is then held in place on the eye 104, and rendered fluid tight with the eye 104, while maintained on the eye 104 in the orientation shown in FIG. 1, by suction that is applied to one or more vacuum chambers.

The reservoir 124, when positioned on the eye 104 and after suction has been applied, can be filled with a fluid having a known index of refraction and thus the index of refraction can be set to match and/or approximate the index of refraction of the glass plate 114 to the index of refraction of the cornea 122.

In operation, a vacuum is formed between device 100 and the surface of the eye 104 by a vacuum source (not shown) that is in communication with a suction entry port 128. The vacuum formed can be so significant as to lift a portion 130 of the conjunctival membrane of the eye 104 into the suction entry port 128. The lifted portion 130 clogs the suction entry port 128, which in turn reduces the vacuum in the vacuum chamber. Such a reduction in vacuum in the vacuum chamber can have adverse effects. For example, proximal to the clog, fluid may drain from the reservoir and air may enter in via channel 132 causing undesirable bubbles to form in the reservoir, which may interfere with the laser beam. Besides the above mentioned draining of fluid, the fluid leaves channel 134 due to capillary action, water adhesion and water cohesion when channel 134 is in contact with an eyelid or cheek skin tissue.

An embodiment of a liquid holding interface device for use in the performance of ophthalmic laser surgery is shown in FIGS. 2-8. The device 200 includes an arm 202 that has an upper end 203 that connects to the laser device (not shown in the figures) and a lower end 204 that includes a ring 206. The arm 202 and ring 206 are preferably made of a unitary material that is reusable and can be sterilized in a doctor's office, such as by use of an autoclave. However, the arm 202 and/or the ring 206 may be made of different materials that are disposable, not autoclavable, and which are not unitary but may be fixedly and/or removably connected together, as well as combinations of such materials.

Figure 2:
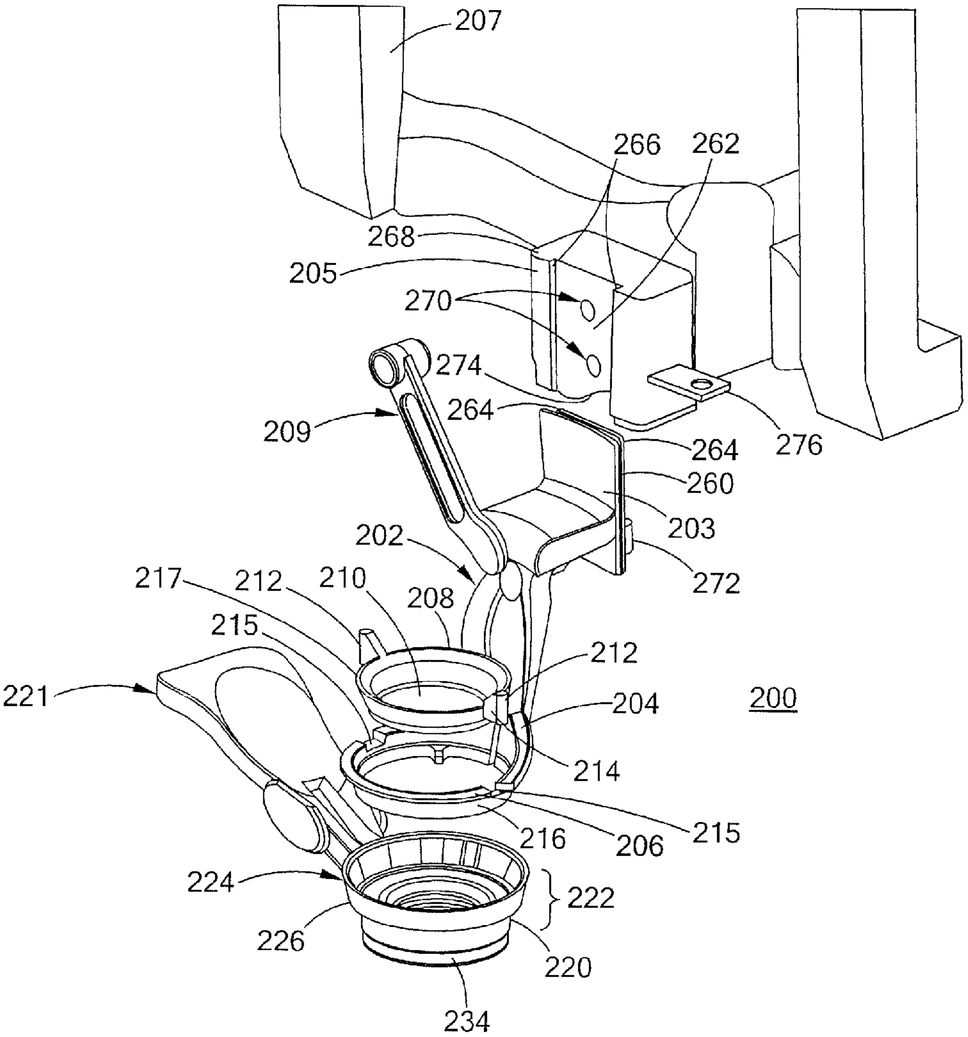
FIG. 2 shows an exploded, perspective view of a portion of an embodiment of a laser device for ophthalmic treatment and a second embodiment of a patient interface device to be used with the laser device in accordance with the present invention.
Figure 3:
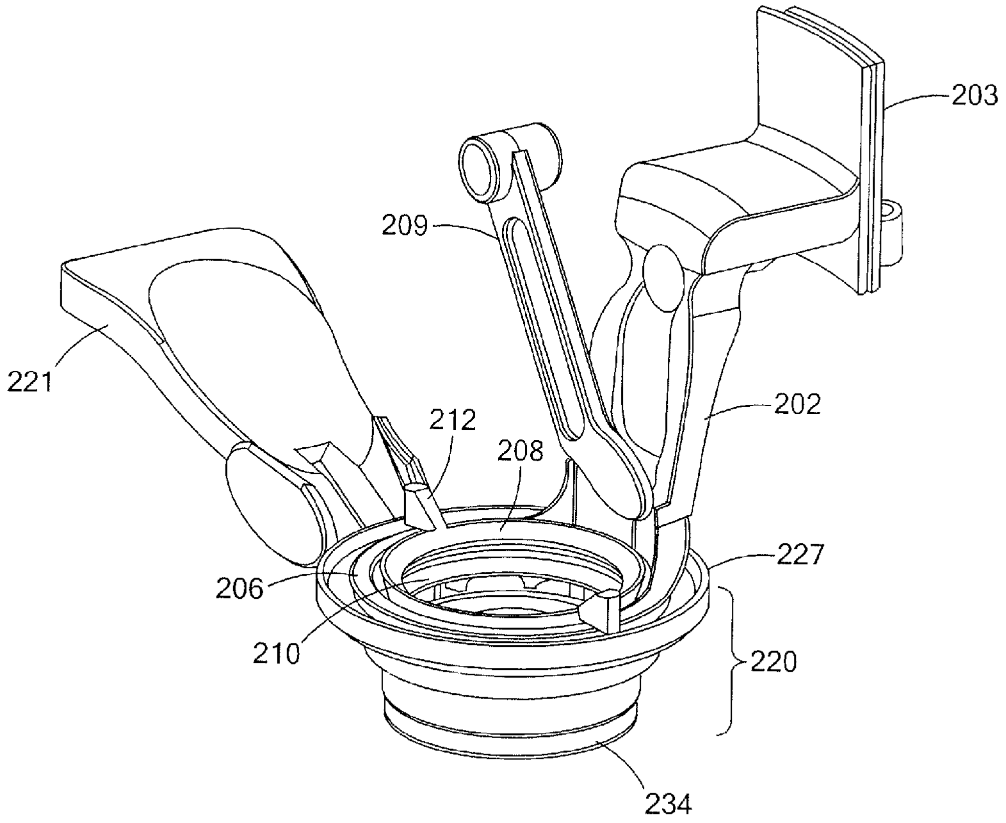
FIG. 3 shows a perspective view of the embodiment of the patient interface device of FIG. 2.

As shown in FIGS. 2-3, the upper end 203 engages a receiving element 205 of a device 207 that includes the laser device. In particular, the upper end 203 includes a male element 260 that is inserted into a slot 262 of the receiving element 205 by having its angled ends 264 inserted into complementary grooves 266 of receiving element 205. The receiving element 205 includes a magnet 268, attached to device 207 via screws 270. The magnet 268 attractively engages magnet 272 of upper end 203, wherein the magnet 272 is snugly fit within gap 274 so that a top end of the magnet 272 abuts a bottom end of magnet 268. When snugly fit, the magnet 272 should snap into place. Once the magnet 272 is snapped into place, a lever 276 is rotated upwards counter-clockwise to a vertical position so as to lock the upper end 203 to the receiving element 205.

The device 200 further has an upper assembly 217 of a liquid holding chamber 242, wherein the upper assembly includes an adapter ring 208 for holding a glass or fused silica plate 210. The plate 210 is attached to the adapter ring 208 via gluing, for example. The adapter ring 208 has a pair of oppositely positioned male extensions 212 that are designed to attach to and hold the adapter ring 208 in the ring 206. Preferably, and by way of example, ramped surfaces 214 of the extensions 212 are inserted into corresponding slots 215 formed in the ring 206, Note that in an alternative embodiment, the slots 215 can be removed and the adapter ring 208 can reach over the continuous ring 206 so as to engage the protruding lip of the ring 206. Another alternative embodiment has the extensions positioned inside the ring which grip corresponding protrusions on the inside of the ring. Then, the adapter ring 208 is rotated so that the ramped surfaces 214 engage the underside of the lip 216 of the ring 206 so that a sufficient frictional attachment between the ring 206 and adapter ring 208 is achieved. Removal of the upper assembly 217 defined by plate 210 and ring 208 is accomplished by rotating the ring 208 in a direction opposite to the rotational direction that accomplished attachment. Note that the structure and function of the ring 206, adapter ring 208 and plate 210 is similar to that described in U.S. Patent Application Publication No. 2011-0022035A1, the entire contents of which are incorporated herein by reference.

The device 200 further includes a lower assembly 220 of the liquid holding chamber 218. As shown in FIGS. 2-3, a handle 221 is attached to the lower suction ring 234, wherein the handle 221 allows a surgeon to position the suction ring 234 on the eye of a patient. As shown in FIGS. 4-6, the lower assembly 220 includes a top retainer 222 that includes a conical-shaped wall 224 that is integrally attached to an annular-like platform 226. As shown in FIG. 4, an exterior wall 227 is attached or integral with an outer surface of the wall 224. An extending portion 229 of the wall 224, an annular base 231 and a vertical wall 233 define a channel 235 to contain excess liquid that will be discussed later. Integrally attached to the bottom of the platform 226 is an inner annular wall 228 and an outer annular wall 230. As shown in FIGS. 5-6, the outer annular wall 230 is continuous except where a cylindrical vacuum port 232 is formed. As shown in FIGS. 4-6, the vacuum port 232 is in fluid communication with a channel 244 and a vacuum source, schematically shown by box 246 of FIG. 4. Thus, a vacuum is formed when vacuum source 246 removes air from the vacuum chamber of the lower assembly 220.

As shown in FIGS. 4-6, a lower suction ring 234 is attached to the inner surface of the outer annular wall 230. In particular, an annular top wall 236 of the low skirt 234 is integrally attached to the inner surface of the outer annular wall 230. As shown in FIGS. 4 and 6, the lower suction ring 234 predominantly has an inverted J-shape for its cross-section, wherein the cross-section has a vertical extending top wall 236, an inward extending annular surface 238 and an L-shaped end shaped portion 240 that wraps about and extends past the inner annular wall 228. The surface 238 and portion 240 are integral with the facing surfaces of the platform 226 and the wall 228, respectively.

As shown in FIGS. 4-6, in the area where the vacuum port 232 is formed, sections of the wall 236, surface 238 and portion 240 are removed. In order to improve suction formed within the chamber a suction enhancer 241 is attached to a shoulder area 244 of the wall 236. The suction enhancer 241 is in the form of a ring that circumscribes the wall 236 and is attached thereto by glue. Of course, in an alternative embodiment the suction enhancer 241 and the wall 236 are integral with one another. The suction enhancer 241 improves the vacuum within the chamber by providing a continuous port or multiple ports to mitigate suction loss via the conjunctive blocking of one or several ports. In addition, the suction enhancer prevents the very soft conjunctival membrane of the eye 104 from sticking and clogging the vacuum port 232, and will keep the vacuum uniform throughout the vacuum chamber.

Figure 7:
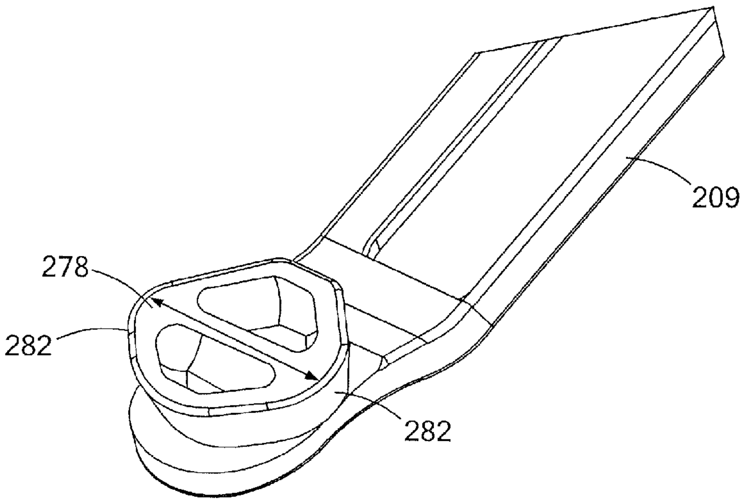
FIG. 7 is a perspective view of an embodiment of a lever used with the patient interface device of FIG. 3.
Figure 8:
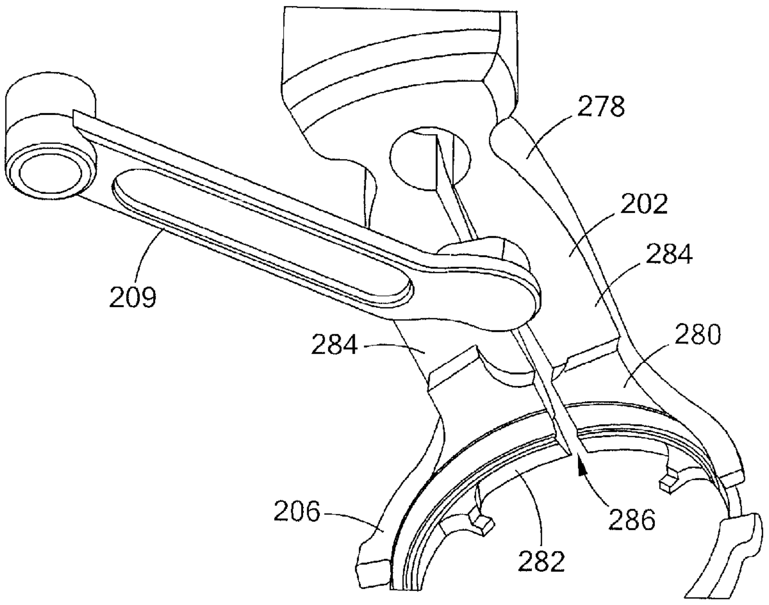
FIG. 8 shows a top perspective view of the lever of FIG. 7 interacting with the arm of the patient interface device of FIG. 3.
Figure 9:
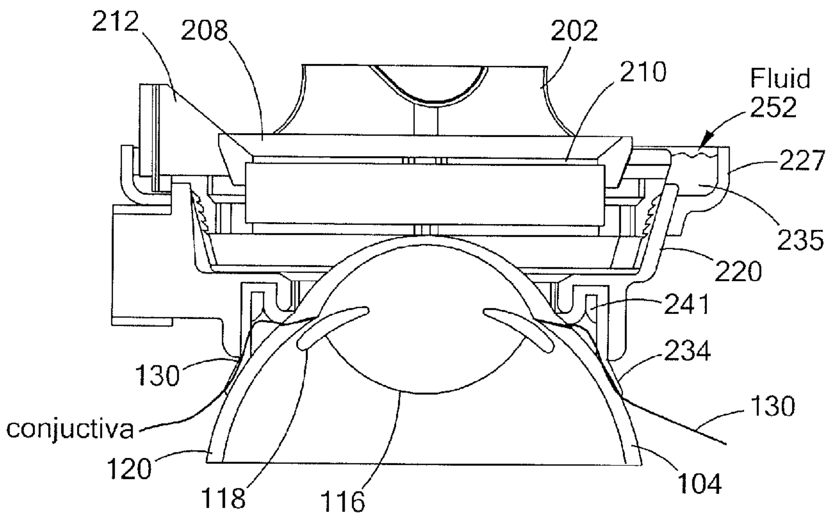
FIG. 9 shows a cross-sectional view of a portion of the patient interface device of FIGS. 2-4.
Figure 10:
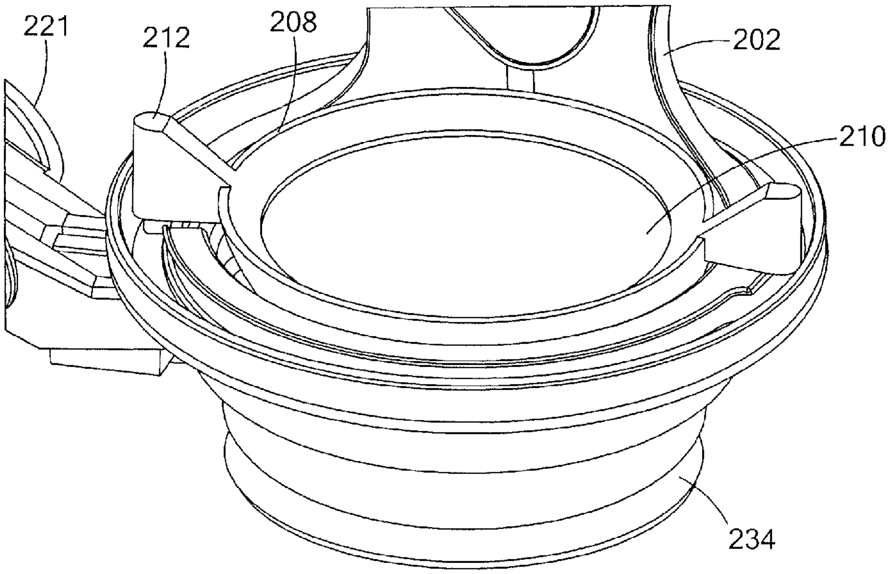
FIG. 10 shows a perspective view of a portion of the patient interface device of FIGS. 2-4.

In operation, when the lower assembly 220 is positioned on the eye, the arm 202, with ring 206 and upper assembly 217 attached thereto, is lowered. During this lowering, the ring 206 is inserted into a mating lip of housing 220. Once inserted into the mating lip, rotation of lever 209 results in clamping attachment of the ring 206 to the housing 220. This clamping attachment is understood upon viewing FIGS. 3, 7 and 8. In particular, FIG. 7 shows that lever 209 has an oblong piece 278 attached at one end. The oblong piece 278 has a minimum width A and a maximum width B. While there is a 45° angle between the maximum and minimum widths, other shapes of the piece 278 and orientations between the maximum and minimum widths are possible. In use the lever starts at 45 degrees from the vertical and is moved to the vertical position to lock. The angle is arbitrary, could be 90 degrees for instance. The oblong piece 278 is inserted into a slot 280 of the arm 202 that has a width that is substantially equal to the minimum width A. The lever 209 is rotated by 45 degrees as shown in FIGS. 3 and 8 so that the minimum width A extends across the width of the slot 280. Next, angled ends 282 of the piece 278 are inserted into complementary grooves 284 of the slot 280. The lever 209 is pushed toward a closed end 282 of the slot 280. As shown in FIG. 8, the arm 202 has a longitudinal slit 286 that allows the ring 206 to be expanded. In particular, when lever 209 is rotated clockwise to a vertical position, the maximum width portion of piece 278 engages the grooves 284 resulting in the slit 286 to become wider and the diameter of the ring 206 to increase. So, when the ring 206 is inserted into the mating lip of the housing 220, the lever 209 is rotated to a vertical clamping position, which results in the ring 206 to expand and contact the top retainer 222 in a clamping manner. As shown in FIG. 4, barbs or protrusions 302 of the ring 206 engage and grab onto the surface of the top retainer 222.

When the above described clamping of the ring 206 with top retainer 222 is combined with the constant downward force (approximately 4 to 12 ounces) of the arm 202, the connection between the assembly 220 and the ring 206 is such that capillary action, adhesion and cohesion produce a small but continuous flow of water.

Note that if there was no lever mechanism so that the ring 206 engages the top retainer 222, then the device would need to rely on the downward force alone to keep the ring 206 and the lower assembly 220 together. Such a configuration would not necessarily lock the ring 206 and lower assembly 220 together and so rocking between the parts could occur. Such rocking would result in unacceptable leaking of fluid. The use of the lever 209 solves this issue of not having a rigid coupling between the ring 206 and the lower assembly 220. Furthermore, the generation of a rigid coupling does not cause any downward force, which could have resulted in a spike of intraocular pressure. With the above said, when a low pressure or partial vacuum is applied to the vacuum chamber via vacuum port 232, the ring 206 is held in place on the eye. While only one vacuum port 232 is used, it is envisioned that multiple vacuum ports can be employed when one or multiple vacuum chambers are employed. In the case of multiple vacuum chambers, they can be separate from one another or they may be in fluid communication with each other, and thus a common vacuum source may be used to apply suction to these chambers and further provide that the amount of suction is equal across all vacuum chambers.

Note that when the lower assembly 220 is positioned on the eye, the free edge of the suction ring 234 engages the eye 104 in a manner similar to that shown in FIG. 1. When the suction ring 234 engages the eye 104 and the vacuum is applied, a secure connection between the lower assembly 220 and the eye 104 is formed. The vacuum also depends on a seal formed between the bottom of the suction ring 234 and the eye 104. In addition, a fluid tight seal is formed between the eye 104 and the lower assembly 220 is formed. As previously mentioned, a fluid tight seal is also formed between the assembly 220 and the ring 206. With the formation of the fluid tight seals mentioned previously, a liquid holding chamber 242 is defined by volume bounded by the outer surface of the eye 104, the upper assembly 217 (including glass plate 210) and the lower assembly 220. As shown in FIGS. 4 and 6, a fluid port 248 for adding and removing fluid from the chamber 242 is formed from the upper assembly 224 and is in fluid communication with a channel 250 and a fluid source, schematically shown by box 252 of FIG. 4. Note that the fluid port 248 may further contain or have associated therewith valves, tubing and suitable fluid deliver components to add, hold and remove fluid from the chamber 242. In addition, a thin annular gap between glass plate 210 and adapter ring 208 exists to allow air and bubbles expelled during the filling of the liquid holding chamber 242 to escape and to avoid obscuration of the therapeutic laser beam by entrapped bubbles.

Note that the fluid can be a fluid of a known index of refraction and thus the index of refraction can be set to match and/or approximate the index of refraction of the lens of the eye 6. Thus, the chamber is preferably filled with a balanced salt solution ("BSS") or saline solution that has been degassed. Moreover, although the preferred embodiment of the present invention is to match or as closely as possible approximate the index of refractions of the device to that of the eye, in other applications having known and predetermined difference may be advantageous. Thus, the reservoir may be filled with a particular index matching fluid having a predetermined and known index of refraction, such as those that are obtainable from NYE and CARGILLE LABS.

Besides the chamber 242, the previously described exterior wall 227 shown in FIGS. 3, 4 and 7 contains a fluid. As shown in FIG. 4, the fluid 252 is contained in the channel 235. Note that the fluid 252 appears in channel 235 when the fluid overflows the top edge 229 during the filling of the main chamber via ports 248/250. The function of the exterior wall 227 is as follows: without a wall 227, fluid in the fluid chamber 242 would flow over the top edge 229 and from the channel 235 via capillary action, water adhesion and cohesion when skin, eyelid or cheek, touches the top edge 229 or upper assembly 217. When the fluid drains, a "bubble" appears under the window. It's not really a bubble, there is just not enough water to then contact the underside of the glass plate. The barrier ring keeps the skin away from the interfaces 229, 217 between the horizontal contact surface at the top edge 229 and the matching horizontal surface under the ring 206. At this interface there are molecular size level gaps that are sufficiently large to allow fluid to escape via capillary action in a manner described elsewhere. Now with the wall 227, top edge 229 and base 231 in place, the fluid is filled into the main chamber 242 via channel 250. The fluid will at times drain from channel 235, not always but when it does, the fluid only drains from channel 235 and the flow will not continue once this fluid volume is gone. The fluid in chamber 242 remains. The flow is stopped by the higher edge, the high surface tension at the corners of surface 229, the weight and cohesion of the water in chamber 242.

Besides aiding in the containment of fluid 252, the wall 227 performs another function. In particular, the vertical wall 233 portion of wall 227 is sufficiently raised so that it will prevent eyebrows or other facial skin tissues from contacting and draining fluid out of channel 235 and fluid chamber 242 via capillary forces.

Disconnection between the assembly 220 and ring 206 is accomplished by lowering the lever 209 and manually removing the two elements from one another. In particular, upon completion of the procedure the vacuum is released, the lever 209 is lowered, and the arm 202 is pulled up away from the suction ring 220. Next, the suction ring 234 is removed from the eye 104 by a surgeon using handle 221, From the foregoing description, one skilled in the art can readily ascertain the essential characteristics of this invention, and without departing from the spirit and scope thereof, can make various changes and/or modifications of the invention to adapt it to various usages and conditions. For example, it is understood that the parts of the device may be integral, unitary, composites, fused or combination of these or other types of materials, as well as combinations of combinations of assemblies and materials, provided that the overall device safely and efficiently accomplishes the objectives of the configuration set forth in FIGS. 2-8.

What is claimed is:

1. A patient interface device for use with a laser surgery apparatus, the device comprising:

a) an upper assembly and a lower assembly;

b) the upper assembly configured to be directly attached to a laser surgery device; the upper assembly comprising a ring for directly engaging the lower assembly; the upper assembly comprising a lever; wherein the ring is configured to clampingly attach to the lower assembly upon a rotation of the lever;

c) the lower assembly comprising a handle for positioning the lower assembly on an eye, wherein the handle is configured so that it does not directly attach to the laser surgery device, and an annular platform and a conical shaped wall at an outer side of the annular platform, the platform and the wall configured for receiving the upper assembly, and a suction ring for engaging the eye; and, d) the suction ring comprising a suction ring wall having an inner surface, and wherein the suction ring wall defines in cross section an inverted J-shape.

2. The patient interface device of claim 1, wherein the upper assembly comprises a plate, and wherein the plate is engaged with the ring.

3. The patient interface device of claim 1, wherein the ring defines an outer surface for engagement with the conical shaped wall of the lower assembly.

4. The patient interface device of claim 1, wherein the upper assembly comprises a plate, and wherein the plate has a central portion configured for direct engagement against the eye, whereby the plate has a radially outward portion configured to not directly contact the eye, when the upper assembly is engaged with the lower assembly and the lower assembly is configured to engage with the eye.

5. The patient interface device of claim 1, wherein the upper assembly comprises a locking arm mechanism, for engaging and locking the upper assembly to the laser surgery device.

6. The patient interface device of claim 1, wherein the upper and lower assemblies are engaged.

7. The patient interface device of claim 6, wherein the device is configured to engage against the eye.

8. The patient interface device of claim 1, wherein the suction ring has a skirt.

9. The patient interface device of claim 8, wherein the skirt is integrally attached to the suction ring wall.

10. The patient interface device of claim 1, wherein the device further comprises a port, wherein the port is configured to provide a fluid.

11. The patient interface device of claim 10, wherein the device further comprises a second port, wherein the second port is configured to provide a vacuum.

12. The patient interface device of claim 1, wherein the device further comprises a port, wherein the port is configured to provide a vacuum.

* * * * *